(12) United States Patent
Maul et al.

(10) Patent No.: US 6,351,999 B1
(45) Date of Patent: Mar. 5, 2002

(54) VORTEX FLOW SENSOR

(75) Inventors: Joachim Maul, Weil/Rhein; Frank Ohle, Steinen, both of (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 09/337,996

(22) Filed: Jun. 22, 1999

Related U.S. Application Data
(60) Provisional application No. 60/100,725, filed on Sep. 17, 1998.

(30) Foreign Application Priority Data
Jun. 25, 1998 (GB) .......................................... 98111663

(51) Int. Cl.⁷ ................................................. G01F 1/32
(52) U.S. Cl. ..................... 73/861.22; 356/351; 356/345
(58) Field of Search ...................... 73/861.22; 356/351, 356/345, 491, 517

(56) References Cited
U.S. PATENT DOCUMENTS

| | | | |
|---|---|---|---|
| 2,813,424 A | | 11/1957 | Liepmann et al. |
| 4,519,259 A | | 5/1985 | Pitt et al. |
| 4,683,760 A | * | 8/1987 | Misumi .................... 73/861.22 |
| 5,011,278 A | * | 4/1991 | Farrell .......................... 356/28 |
| 5,420,687 A | * | 5/1995 | Kachanov .................... 356/353 |
| 5,604,591 A | * | 2/1997 | Kitagawa .................... 356/351 |

FOREIGN PATENT DOCUMENTS
GB 2 084 720 4/1982

* cited by examiner

*Primary Examiner*—Max Noori
*Assistant Examiner*—Corey D. Mack
(74) *Attorney, Agent, or Firm*—Bose McKinney & Evans LLP

(57) ABSTRACT

This sensor for measuring the flow velocity and/or the flow rate of a fluid provides an optical sensor system which is also suitable for use at temperatures higher than 400° C., does not come into contact with the fluid, and requires less space than conventional optical sensor systems. The sensor comprises a tube (1) through which the fluid flows in a first direction and which has a wall (11) in which a first window (2) and a second window (3) of optical, schlieren-free, high-temperature glass are set fluid-tight and pressure-tight at points lying opposite each other along a first tube diameter. A bluff body (4) is disposed along a second tube diameter and fixed in the tube for generating Kármán vortices, whose frequency f is proportional to the flow velocity u. The second diameter is up-stream of, and perpendicular to, the first. A laser differential interferometer (6, 6') has a transmitting unit (61, 61') mounted outside the tube in front of the first window and fixed thereto and comprises optical components, which follow one another in the direction to the first window: a laser (21, 31), a lens system (22, 32), a first polarization filter (23), a first Wollaston prism (24, 34), and a first lens (25, 35). A receiving unit (62, 62') is mounted outside the tube in front of the second window and fixed thereto and comprises the optical components, which fellow one another in a direction away from the second window: a second lens (26, 36), a second Wollaston prism (27, 37), a second polarization filter (28), and a PIN diode (29, 39).

4 Claims, 1 Drawing Sheet

VORTEX FLOW SENSOR

This appln claims benefit of Prov. No. 60/100,725 filed Sep. 17, 1998.

BACKGROUND OF THE INVENTION

This invention relates to vortex flow sensors for measuring the flow velocity and/or the volumetric flow rate of a fluid flowing in a measuring tube.

Conventional vortex flow sensors have a bluff body which is disposed along a diameter of the measuring tube and fixed in the wall of this tube.

During operation of such a vortex flow sensor, as is well known, a Karman vortex street is formed downstream of the bluff body. Its pressure fluctuations are converted by a sensing element into an electric signal whose frequency is proportional to the fluid velocity, from which the volumetric flow rate can be calculated.

The vortex sensing elements used so far are, on the one hand, devices which extend into the fluid and on which the pressure fluctuations act directly; such devices are, for example, pressure sensors, particularly capacitive ones, which are mounted in the bluff body or which are mounted in or inserted through the wall of the measuring tube down-stream of the bluff body.

On the other hand, the pressure fluctuations have been measured by means of an ultrasonic arrangement whose transmitter and receiver are mounted outside the measuring tube diametrically opposite each other. The transmitter sends ultrasonic signals through the wall of the measuring tube, the fluid, and the opposite wall which are modulated by the pressure fluctuations and registered by the receiver.

Each of these two types of sensing elements has inherent disadvantages which preclude vortex flow sensors fitted with such sensing elements from being used with any fluid. Ultrasonic sensors can be used only up to fluid temperatures of approximately 250° C., and capacitive pressure sensors only up to fluid temperatures of approximately 400° C.

Furthermore, vortex flow sensors have been described in which a light or laser beam is sent through the fluid and the intensity modulation of the beam by the vortices serves to determine the vortex frequency; see, for example, U.S. Pat. No. 4,519,259 or GB-A 2,084,720. Such optical vortex flow sensors also withstand temperatures higher than 400° C.

SUMMARY OF THE INVENTION

It is an object of the invention to provide an optical sensor system which is also suitable for use at temperatures higher than 400° C., does not come into contact with the fluid, and requires less space than conventional optical sensor systems.

To attain this object, a first variant of the invention provides a vortex flow sensor for measuring the flow velocity and/or the volumetric flow rate of a fluid, said vortex sensor comprising:
  a measuring tube
    through which the fluid flows in a first direction and
    which has a wall in which a first window and a second window of optical, schlieren-free, high-temperature glass are set fluid-tight and pressure-tight at points lying opposite each other along a first diameter of the measuring tube;
  a bluff body disposed along a second diameter of the measuring tube and fixed in the measuring tube for generating Kármán vortices in the fluid, whose frequency is proportional to the flow velocity,
    said second diameter lying upstream of, and being essentially perpendicular to, the first diameter; and
  a laser differential interferometer having
    a transmitting unit mounted outside the measuring tube in front of the first window and fixed to the first window and/or the measuring tube, said transmitting unit comprising the following optical components, which follow one another in the direction to the first window:
      a laser,
      a lens system,
      a first polarization filter,
      a first Wollaston prism, and
      a first lens, and
    a receiving unit mounted outside the measuring tube in front of the second window and fixed to the second window and/or the measuring tube, said receiving unit comprising the following optical components, which follow one another in a direction away from the second window:
      a second lens,
      a second Wollaston prism,
      a second polarization filter, and
      a PIN diode.

To attain the above object, a second variant of the invention provides a vortex flow sensor for measuring the flow velocity and/or the volumetric flow rate of a fluid, said vortex sensor comprising:
  a measuring tube
    through which the fluid flows in a first direction and
    which has a wall in which a first window and a second window of optical, schlieren-free, high-temperature glass are set fluid-tight and pressure-tight at points lying opposite each other along a first diameter of the measuring tube;
  a bluff body disposed along a second diameter of the measuring tube and fixed in the measuring tube for generating Kármán vortices in the fluid, whose frequency is proportional to the flow velocity,
    said second diameter lying upstream of, and being essentially perpendicular to, the first diameter; and
  a laser differential interferometer having
    a transmitting unit mounted outside the measuring tube in front of the first window and fixed to the first window and/or the measuring tube, said transmitting unit comprising the following optical components, which follow one another in the direction to the first window:
      a laser emitting polarized light,
      a lens system,
      a first Wollaston prism, and
      a first lens, and
    a receiving unit mounted outside the measuring tube in front of the second window and fixed to the second window and/or the measuring tube, said receiving unit comprising the following optical components, which follow one another in a direction away from the second window:
      a second lens,
      a second Wollaston prism,
      a polarization filter, and
      a PIN diode.

In a preferred embodiment of the first or second variant of the invention, the first and second lenses are achromats.

One advantage of the invention is that even fluids having a temperature of, e.g., 600° C. can be measured on the vortex principle.

Another advantage results from the fact that the optical components can be fabricated using microsystem technology, so that the optical sensor system takes up less space than conventional sensor systems.

BRIEF DESCRIPTION OF THE DRAWINGS

The invention will become more apparent from the following description of embodiments when taken in conjunction with the accompanying schematic drawing, in which.

DETAILED DESCRIPTION OF THE PREFERRED EMBODIMENTS

Figure 1:
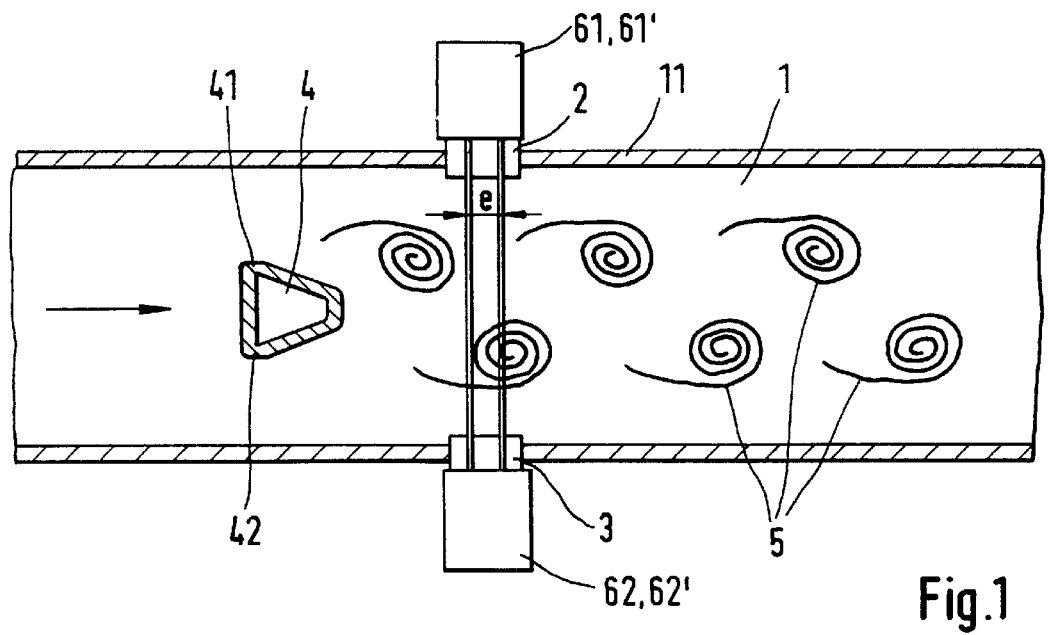
FIG. 1 shows a longitudinal section of the measuring tube with the vortex flow sensor.

Referring to FIG. 1, there is shown a schematic longitudinal section of a measuring tube 1 through which a fluid whose volumetric flow rate and/or flow velocity are/is to be measured is flowing in the direction indicated by the arrow. The fluid may be a liquid, a gas, or a vapor.

The measuring tube 1 has a wall 11 in which a first window 2 and a second window 3 are set fluid-tight and pressure-tight. The two windows 2, 3 are made of an optical, schlieren-free and bubble-free, high-temperature glass and are fitted in the wall 11 at opposite points along a first diameter of the measuring tube 1 such that their internal surfaces are as flush with the internal surface of the measuring tube as possible.

Along a second diameter, a bluff body 4 is fixed in the measuring tube 1. The second diameter lies upstream of, and is essentially perpendicular to, the first diameter. The bluff body 4 serves to generate Kármán vortices 5 in the fluid, which are shed from the bluff body alternately from a left-hand shedding edge 41 and a right-hand shedding edge 42, as viewed in the direction of flow. The frequency f of vortex shedding, as is well known, is proportional to the flow velocity u and the cross section A of the lumen of the measuring tube 1; from these quantities, the volumetric flow rate Q can be calculated:

$$Q=uA \quad u=kf \quad Q=kAf,$$

wherein k is a constant to be measured during a calibration step of the vortex flow meter.

A laser differential interferometer 6 (see FIG. 2) or 6' (see FIG. 3) has a transmitting unit 61 or 61' and a receiving unit 62 or 62' disposed outside the measuring tube 1, the transmitting unit being located in front of the window 2 and the receiving unit in front of the window 3.

The transmitting unit and the receiving unit are fixed to the windows 2 and 3, respectively, and/or to the measuring tube 1, so that relative movements between the measuring tube and the transmitting and receiving units, which would result in spurious signals, are avoided.

Figure 2:
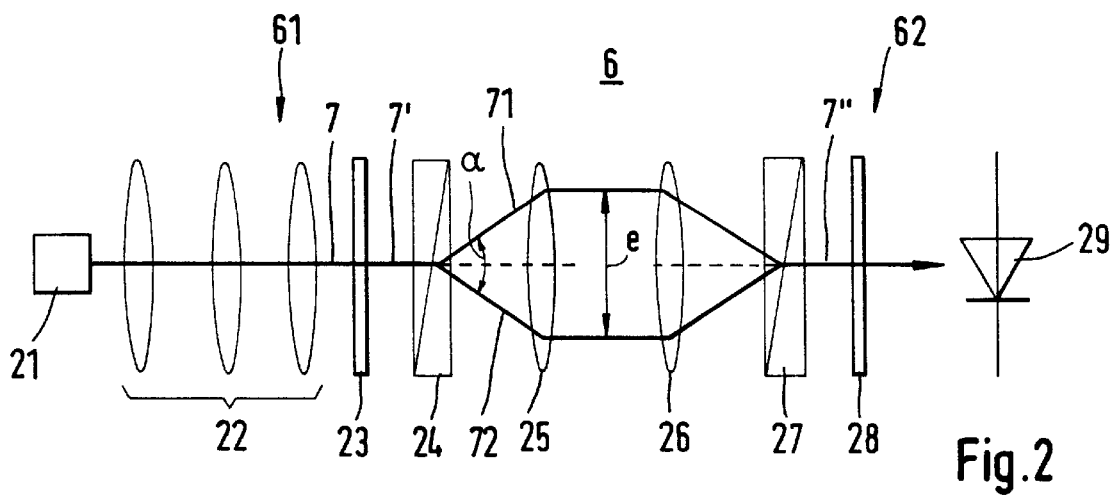
FIG. 2 shows individual components of a laser differential interferometer and the associated beam path according to the first variant of the invention.

FIG. 2 shows schematically individual components of the laser differential interferometer 6 and the associated beam path in accordance with the first variant of the invention. In the direction of the window 2, the following optical components of the transmitting unit 61 are arranged in succession: a laser 21, a first lens system 22, a first polarization filter 23, a first Wollaston prism 24, and a first lens 25, preferably an achromat.

The lens system 22 focuses the light emitted by the laser in the form of a beam 7 onto the polarization filter 23, which passes only components vibrating in the same plane, i.e., components in the form of a polarized beam 7'. The latter impinges on the Wollaston prism 24, which divides it into first and second orthogonally polarized beams 71, 72, which form an angle α. The lens 25 causes the two beams to pass through the fluid in parallel, with the two beams being separated by a distance e.

After passing through the fluid, the two beams 71, 72 reach the receiving unit 62. In a direction away from the window 3, the following optical components of the receiving unit 62 are arranged in succession: a second lens 26, preferably an achromat, a second Wollaston prism 27, a second polarization filter 28, and a PIN diode 29.

After passing through the fluid, the two beams 71, 72 are recombined into a single beam 7" by means of the lens 26 and the Wollaston prism 27, and heterodyned by means of the polarization filter 28, whereby phase differences are produced, as is well known. These are converted by the PIN diode 29 into electric signals whose frequency can be easily determined by means of suitable frequency evaluation electronics. As such electronics are known and commercially available, they will not be explained here.

Figure 3:
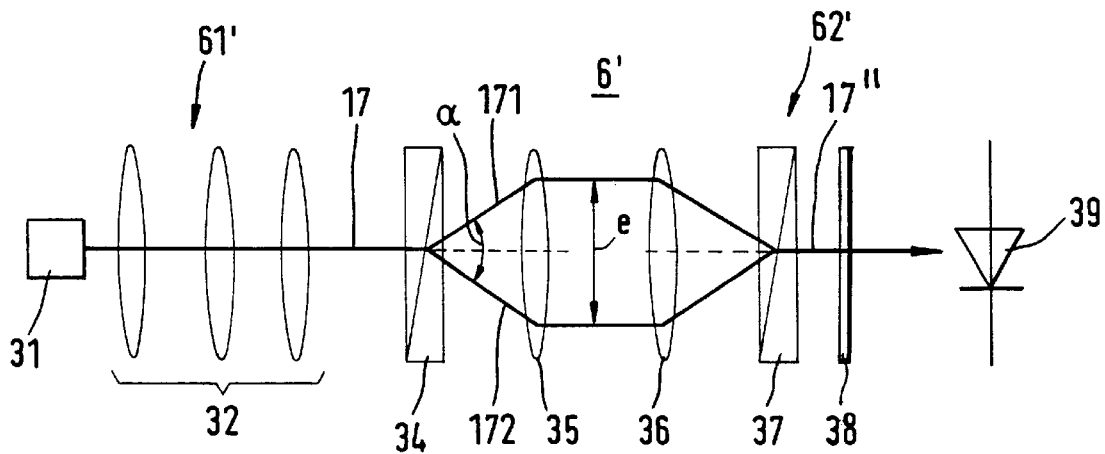
FIG. 3 shows individual components of a laser differential interferometer and the associated beam path according to the second variant of the invention.

FIG. 3 shows schematically individual components of the laser differential interferometer 6' and the associated beam path in accordance with the second variant of the invention. In the direction of the window 2, the following optical components of the transmitting unit 61' are arranged in succession: a laser 31 emitting polarized light, a lens system 32, a first Wollaston prism 34, and a first lens 35, preferably an achromat.

In comparison with FIG. 2, because of the laser 31 already emitting polarized light, a polarization filter corresponding to polarization filter 23 is not necessary and, therefore, not present. The lens system 32 thus focuses the light emitted by the laser 31 in the form of a polarized beam 17 directly onto the Wollaston prism 34, which divides it into first and second orthogonally polarized beams 171, 172, which again form an angle α, and which are again separated by a dis-tance e after the lens 35.

After passing through the fluid, the two beams 171, 172 reach the receiving unit 62'. In a direction away from the window 3, the following optical components of the receiving unit 62' are arranged in succession: a second lens 36, a second Wollaston prism 37, a polarization filter 38, and a PIN diode 39.

After passing through the fluid, the two beams 171, 172 are recombined into a single beam 17" by means of the lens 36 and the Wollaston prism 37, and heterodyned by means of the polarization filter 38. The resulting phase differences are converted by the PIN diode 39 into electric signals whose frequency can be easily determined by means of suitable frequency evaluation electronics.

In the invention, periodic changes in the density d of the fluid which are caused along the path of the laser light by the vortices 5 shedding from the bluff body 4 are optically evaluated. The measurement limit attainable with the invention is determined by the resolution g of the laser differential interferometer:

$$g=\delta d/e,$$

where δd is the instantaneous density gradient along the optical path of the laser light of the two beams 71, 72 or 171, 172.

The density d can be calculated from the Lorentz-Lorenz equation:

$$d=(n^2-1)/R(n^2+2),$$

where n is the index of refraction and R is the specific refractivity of the fluid, which is dependent on the light wavelength $l$.

For air and a wavelength value of $l=632$ nm, for example, the refractivity has a value of $R=0.0000152$ m$^3$/kg. Since the refractivity R varies over a wide pressure and temperature range by only about 3%, it may be assumed to be constant.

The above Lorentz-Lorenz equation can be simplified, since only the aforementioned density gradients δd occur and since the resulting variations δn in the index of refraction are small:

$$\delta d/\delta n = 6n/R(n^2+2)^2.$$

Furthermore, $$\delta n = 1/D,$$

where D is the diameter of the measuring tube $l$.

For $l=632$ mm, $e=2$ mm, and $D=53$ mm, a resolution of $g=0.00262$ kg/(m$^3$mm) is obtained. If the fluid to be measured is a gas, this resolution is already sufficient for flow velocities above 2 m/s.

What is claimed is:

1. A vortex flow sensor for measuring at least one of the flow velocity and the volumetric flow rate of a fluid, said vortex sensor comprising;

a measuring tube;
   through which the fluid flows in a first direction and which has a wall in which a first window and a second window of optical, schlieren-free, high temperature glass are set fluid tight and pressure tight at points lying opposite each other along a first diameter of the measuring tube;

a bluff body disposed along a second diameter of the measuring tube and fixed in the measuring tube for generating Kármán vortices in the fluid, whose frequency is proportional to the flow velocity, said second diameter lying upstream of, and being essentially perpendicular to, the first diameter; and a laser differential interferometer having a transmitting unit mounted outside the measuring tube in front of the first window and fixed to at least one of the first window and the measuring tube, said transmitting unit comprising the following optical components, which follow one another in the direction to the first window;

a laser, a lens system, a first polarization filter, a first Wollaston prism, and a first lens, and a receiving unit mounted outside the measuring tube in front of the second window and fixed to at least one of the second window and the measuring tube, said receiving unit comprising the following optical components, which follow one another in a direction away from the second window;

a second lens, a second Wollaston prism, a second polarization filter, and a PIN diode.

2. A vortex flow sensor for measuring at least one of the flow velocity and the volumetric flow rate of a fluid, said vortex sensor comprising;

a measuring tube through which the fluid flows in a first direction and which has a wall in which a first window and a second window of optical, schlieren-free, high temperature glass are set fluid tight and pressure tight at points lying opposite each other along a first diameter of the measuring tube;

a bluff body disposed along a second diameter of the measuring tube and fixed in the measuring tube for generating Kármán vortices in the fluid, whose frequency is proportional to the flow velocity, said second diameter lying upstream of, and being essentially perpendicular to, the first diameter; and a laser differential interferometer having a transmitting unit mounted outside the measuring tube in front of the first of the front window and fixed to at least one of the first window and the measuring tube, said transmitting unit comprising the following optical components, which follow one another in the direction to the first window: a laser emitting polarized light, a lens system, a first Wollaston prism, a first lens, and a receiving unit mounted outside the measuring tube in front of the second window and fixed to at least one of the second window and the measuring tube, said receiving unit comprising the following optical components, which follow one another in a direction away from the second window: a second lens, a second Wollaston prism, a polarization filter, and a PIN diode.

3. A vortex flow sensor as claimed in claim 1 wherein the first and second lenses are achromats.

4. A vortex flow sensor as claimed in claim 2 wherein the first and second lenses are achromats.

* * * * *

UNITED STATES PATENT AND TRADEMARK OFFICE
CERTIFICATE OF CORRECTION

PATENT NO. : 6,351,999 B1 Page 1 of 1
DATED : March 5, 2002
INVENTOR(S) : Joachim Maul and Frank Ohle It is certified that error appears in the above-identified patent and that said Letters Patent is hereby corrected as shown below:

<u>Title page,</u>
Item [56], References Cited, add the following cited reference to the "OTHER PUBLICATIONS" section:

-- Althaus, W., "Experimental investigation of vortex, formation in the wake of a flat plate for subsonic and supersonic freestream Mach numbers, July 9, 1990, 8212 Experiments in Fluids, Berlin, DE pp. 267-272. --

Signed and Sealed this

Tenth Day of September, 2002

*Attest:*

*Attesting Officer*

JAMES E. ROGAN
*Director of the United States Patent and Trademark Office*